US008557531B2

(12) United States Patent
Lorence (10) Patent No.: US 8,557,531 B2
(45) Date of Patent: Oct. 15, 2013

(54) DETECTION OF CIRCULATING ENDOTHELIAL CELLS

(75) Inventor: Robert M. Lorence, Brookfield, CT (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 621 days.

(21) Appl. No.: 12/296,476

(22) PCT Filed: Apr. 18, 2007

(86) PCT No.: PCT/US2007/066856
§ 371 (c)(1),
(2), (4) Date: Oct. 8, 2008

(87) PCT Pub. No.: WO2007/121464
PCT Pub. Date: Oct. 25, 2007

(65) Prior Publication Data
US 2009/0170129 A1 Jul. 2, 2009

Related U.S. Application Data

(60) Provisional application No. 60/745,014, filed on Apr. 18, 2006.

(51) Int. Cl.
| *A01N 1/02* | (2006.01) |
| *G01N 33/567* | (2006.01) |
| *G01N 1/30* | (2006.01) |
| *G01N 1/18* | (2006.01) |

(52) U.S. Cl.
USPC ............ 435/7.21; 435/2; 435/7.24; 435/40.5; 435/371; 435/372; 435/287.2; 436/518; 436/523; 436/526; 436/10; 436/63; 436/164; 436/175; 436/177; 422/52; 422/82.01

(58) Field of Classification Search
USPC .......... 435/2, 7.1, 7.21, 7.23, 7.24, 40.5, 371, 435/372, 287.2; 436/518, 523, 526, 536, 436/10, 64, 149, 164, 177, 63, 175; 422/52, 422/73, 82.01, 98
See application file for complete search history.

(56) References Cited

U.S. PATENT DOCUMENTS

| 7,820,373 B2 | 10/2010 | Hess et al. |
| 2002/0172987 A1 | 11/2002 | Terstappen et al. |

(Continued)

FOREIGN PATENT DOCUMENTS

| WO | 00/52474 A1 | 9/2000 |
| WO | WO 00/52474 * | 9/2000 |

(Continued)

OTHER PUBLICATIONS

Richter, "Electrochemiluminescence (ECL)", Chemical Reviews, 104: 3003-3036, 2004.

(Continued)

*Primary Examiner* — Gail R Gabel
(74) *Attorney, Agent, or Firm* — Lewis J. Kreisler (57) ABSTRACT

Endothelial cells are detected in a blood sample by enriching the endothelial cells from the blood sample followed by performing on the enriched endothelial cells an immunoassay capable of detecting antigens expressed by the endothelial cells. The immunoassay is capable of detecting antigen expressed from 300 endothelial cells per milliliter of blood. The method can be used for assaying mature circulating endothelial cells or circulating endothelial progenitor cells.

10 Claims, 6 Drawing Sheets

(56) References Cited

U.S. PATENT DOCUMENTS

| | | | |
|---|---|---|---|
| 2004/0110241 A1* | 6/2004 | Segal | 435/7.21 |
| 2005/0244897 A1* | 11/2005 | Zeiher et al. | 435/7.2 |
| 2008/0214623 A1 | 9/2008 | Chandi et al. | |
| 2008/0261243 A1 | 10/2008 | Lorence et al. | |

FOREIGN PATENT DOCUMENTS

| | | | |
|---|---|---|---|
| WO | 03/006104 A2 | | 1/2003 |
| WO | WO 2004/008099 | * | 1/2004 |
| WO | 2006/041959 | | 4/2006 |

OTHER PUBLICATIONS

Pending (as of Oct. 8, 2008) claims from U.S. Appl. No. 12/296,458.
Pending (as of Oct. 16, 2008) claims from U.S. Appl. No. 12/297,420.
Woywodt, et al., "Circulating endothelial cells as markers for ANCA-associated small-vessel vasculitis", The Lancet, 361: 206-210, Jan. 2003.
Woywodt, et al., "Elevated Numbers of Circulating Endothelial Cells in Renal Transplant Recipients", Transplantation,76(1): 1-4, Jul. 2003.
"White blood cell", Wikipedia, http://en.wikipedia.org/wiki/white_blood_cell, (downloaded on Apr. 20, 2009).
Database EMBASE, Accession No. 2007289244, Xie S, et al., "Isolation, culture, and biological characteristics of endothelial progenitor cells from human umbilical cord blood CD133+ cells", Journal of Clinical Rehabilitative Tissue Engineering Research, 11(7): 1287-1289, 2007. (Abstract).
Database MEDLINE, Accession No. 2006120503, Shaffer, et al., "Flow cytometric measurement of circulating endothelial cells: the effects of age and peripheral arterial disease on baseline levels of mature and progenitor populations", Cytomerty, Part B, Clinical Cytomerty, 70(2): 55-62, 2006. (Abstract).
Vona, et al., "Isolation by Size of Epithelial Tumor Cells: A New Method for the Immunomorphological and Molecular Characterization of Circulating Tumor Cells", American Journal of Pathology, 156(1): 57-63, 2000.
Lee, et al., "Development and Application of a Quantitative, Specific Assay for *Cryptosporidium parvum* Oocyst Detection in High-Turbidity Environmental Water Samples", Am. J. Trop. Med. Hyg., 65(1): 1-9, 2001.
Liu, et al., "Rapid Detection of *Escherichia coli* O157:H7 Inoculated in Ground Beef, Chicken Carcass, and Lettuce Samples with an Immunomagnetic Chemiluminescence Fiber-Optic Biosensor", Journal of Food Protection, 66(3): 512-517, 2003.
Yu, et al., "Detection of biological threat agents by immunomagnetic microsphere-based solid phase fluorogenic- and electro-chemiluminescence", Biosensors & Bioelectronics,14: 829-840, 2000.
Howanitz, "Immunoassay: Innovations in Label Technology", Arch. Pathol. Lab. Med., 112:775-779, 1988.
Butcher, et al., "A sensitive time-resolved fluorescent immunoassay for metallothionein protein", Journal of Immunological Methods, 272: 247-256, 2003.
Soukka, et al., "Supersensitive Time-resolved Immunofluorometric Assay of Free Prostate-specific Antigen with Nanoparticle Label Technology", Clinical Chemistry, 47(7): 1269-1278, 2001.
Beaudry, et al., "Differential Effects of Vascular Endothelial Growth Factor Receptor-2 Inhibitor ZD6474 on Circulating Endothelial Progenitors and Mature Circulating Endothelial Cells: Implications for Use as a Surrogate Marker of Antiangiogenic Activity", Clinical Cancer Research, 11(9) 2005.
Beerepoot, et al., "Increased levels of viable circulating endothelial cells are an indicator of progressive disease in cancer patients", Annals of Oncology 15: 139-145, 2004.
Davis, et al., "Surrogate markers in antiangiogenesis clinical trial", British Journal of Cancer, 89:8-14, 2003.
Hill, et al., "Circulating Endothelial Progenitor Cells, Vascular Function, and Cardiovascular Risk", New England Journal of Medicine, 348(7):593-600, 2003.
Khan, et al., "Detection of Circulating Endothelial Cells and Endothelial Progenitor Cells by Flow Cytometry",Cytometry Part B (Clinical Cytometry) 64B:1-8 (2005).
Mancuso, et al., "Resting and activated endothelial cells are increased in the peripheral blood of cancer patients", Blood, 97(11): 3658-3661, 2001.
Rosenzweig, "Circulating Endothelial Progenitors—Cells as Biomarkers", New England Journal of Medicine, 353(10): 1055-1057, 2005.
Schmidt-Lucke, et al., "Reduced Number of Circulating Endothelial Progenitor Cells Predicts Future Cardiovascular Events", Circulation,111: 2981-2987, 2005.
Werner, et al., "Circulating Endothelial Progenitor Cells and Cardiovascular Outcomes", New England Journal of Medicine, 353(10):999-1007, 2005.
Zhang, et al., "Protein quantification from complex protein mixtures using a proteomics methodology with single-cell resolufion", PNAS, 98(10): 5497-5502, May 2001.
Blackburn, et al., "Electrochemiluminescence Detection for Development of Immunoassays and DNA Probe Assays for Clinical Diagnostics", Clinical Chemistry, 37(9): 1534-1539, 1991.
Yu, et al., "Comparative studies of magnetic particle-based solid phase fluorogenic and electrochemiluminescent immunoassay", Journal of Immunological Methods, 218:1-8, 1998.
Yuan, et al., "Sandwich-type electrochemiluminescence immunosensor based on RU-silica@ Au composite nanoparticles labeled anti-AFP", Talanta, 82: 1468-1471, 2010.

* cited by examiner

DETECTION OF CIRCULATING ENDOTHELIAL CELLS

BACKGROUND OF THE INVENTION

There are two distinct populations of circulating endothelial cells: bone marrow derived circulating endothelial progenitors (CEPs) and mature circulating endothelial cells (mCECs) (Beaudry et al., 2005, Clin Cancer Res 11:3514; For additional background see Rosenzweig, 2005; New Engl J Med 353:1055-1057; Khan SS, 2004; Cytometry Part B, Clinical Cytometry 64B: 1-8). Measurement of circulating endothelial cells can act as surrogate markers for biological activity of antiangiogenic agents and used to select patients who will benefit from such therapy for cancer (Beaudry et al., 2005, Clin Cancer Res.). For example, patients with CEPs expressing high levels of VEGFR are excellent candidates for treatment with VEGFR inhibitors such as bevacizumab (Avastin). Also, measurement of mCECs is useful in cancer since an increased level indicates disease progression (Mancuso P et al., 2001, Blood 97:3658-61; Beerepoot L V et al, 2004, Ann Oncol 15:139-45).

But "The clinical testing of these [antiangiogenic] agents is currently hampered, by the lack of surrogate markers for measuring their biological effect and predicting which patients are most likely to benefit." (Davis D W, et al., 2003, Br J Cancer 89:8-14). Therefore there is a need for a test to predict which cancer patients will likely benefit from antiangiogenic therapy.

Circulating endothelial cells are an important prognostic factor in cardiovascular field of medicine. Low levels of CEPs indicate a high risk of cardiovascular events (Hill J M et al, 2003, New Engl J Med 348:593-600; Werner N, et al., 2005, New Engl J Med 353:999-1007; Schmidt-Lucke C et al., Circulation 2005, 111:2981-87). There is a need for a test to better predict which patients are at risk for cardiovascular events. In a patient suspected of having a myocardial infarction (MI), high levels of CEPs suggest the recent occurrence of an MI. There is a need for a better test to predict which patients have had a myocardial infarction if they are suspected of having had one.

The approaches used in the published literature to quantify CEPs and mCECs often use flow cytometry (Werner N et al., 2005, N Engl J Med 353:999-1007) which is described as a "difficult undertaking" (Khan SS et al., 2004). This is a cumbersome and time-consuming approach not readily amenable to automation. A further problem with flow cytometry et al is the high background staining in flow cytometry. Nonspecific staining of 0.1 to 0.5% of cells analyzed is commonly seen with flow cytometry and this is too high and will mask the detection and numeration of the desired circulating endothelial cell population which can be as low as 0.0001% (Khan SS et al. (2004; Cytometry Part B, Clinical Cytometry 64B: 1-8)). Excessive data storage capacity is another problem with rare event analysis by flow cytometry (Khan et al., 2004). Another method used in the literature to measure CEPs is by colony counting (Hill J M et al., 2003, New Engl J Med 348:593-600). This method is slower than flow cytometry taking more than one week to perform (Hill et al., 2003). The method of this invention therefore is a significant advance in the field in that it allows for a rapid assessment of circulating endothelial cells and avoids the difficulties (background issues, excessive data storage capacity) inherent in a rare event analysis by flow cytometry.

CEPs and mCECs represent a very small fraction of mononuclear cells in the blood with an estimate of between 0.01% and 0.0001% (Khan SS et al., 2004). Enumeration of these cells in the peripheral blood is important medically because they provide an insight into the body's angiogenic and neovasculogenic activities. Angiogenesis has been shown to be critical for tumor growth and novel anti-angiogenic therapies (such as the approved agent bevacizumab) are used to slow or prevent tumor growth. Angiogenesis and neovascularization are also detrimental in many other diseases besides cancer, including sickle cell disease, vasculitidis, and pulmonary hypertension (Khan SS et al., 2004). In contrast, in coronary artery disease, neovascularization or revascularization is desirable in order to improve blood flow to the cardiac tissue.

SUMMARY OF THE INVENTION

This invention provides a method of assaying endothelial cells in a blood sample comprising enriching the endothelial cells from the blood sample followed by performing on the enriched endothelial cells an immunoassay capable of detecting antigen expressed by three hundred endothelial cells per ml of blood sample. Alternatively the assay is capable of detecting the antigen from one hundred sixty picograms of antigenic protein.

This invention provides a method of assaying an endothelial cell antigen on endothelial cells in a blood sample comprising enriching the endothelial cells from the blood sample followed by performing on the enriched endothelial cells an immunoassay capable of detecting the antigen expressed by the endothelial cells; wherein the immunoassay has a sensitivity defined by being capable of detecting the antigen from three hundred endothelial cells per milliliter of blood or by being capable of detecting the antigen from one hundred sixty picograms of antigenic protein; and wherein the immunoassay generates a signal proportional to the amount (i.e. numbers) of the antigen on the endothelial cells.

This invention provides immunoassays sensitive enough for quantifying the levels of circulating endothelial cells (mCECs and/or CEPs) in blood samples. These immunoassays provide methods of identifying patients at increased risk from various diseases (e.g., cancer, sickle cell disease, vasculitidis, diabetes, pulmonary hypertension, and cardiovascular disease).

BRIEF DESCRIPTION OF THE FIGURES

Compared to FIGS. 1 and 2, this FIG. 3 presents additional data from PBMCs. For comparison purposes, the same data from the HUVEC cells from FIGS. 1 and 2 are also presented.

DETAILED DESCRIPTION OF THE INVENTION

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

As used herein to "enrich" a given kind of cells from a sample means to purify or partially purify such cells from other kinds of cells in the sample.

ABBREVIATIONS mCEC: mature circulating endothelial cell
CEP: circulating endothelial progenitor
ECL: electrochemiluminescence
HUVEC: human umbilical vein endothelial cell
MI: myocardial infarction
PBMCs: peripheral blood mononuclear cells
VEGF: vascular endothelial growth factor
VEGFR2: vascular endothelial growth factor receptor-2

CEPs can be distinguished due to the presence of the following markers (Khan et al., 2004; Rosenzweig, 2005, New Engl J Med 353:1055-7):
  CD133 (not present on mCECs)
  VEGFR-2 (vascular cell adhesion molecule-1; also called KDR)
  CD34
  Lack of CD45 and lack of CD3
mCECs can be distinguished due to the presence of the following markers:
  CD146 (not present on CEPs)
  Von Willebrand factor (vWF)
  CD31 (also called PECAM-1: platelet endothelium cell adhesion molecule-1)
  Lack of CD45 and lack of CD3 (this is important since activated T cells can express CD146; Khan et al., 2004).

This invention provides immunoassays sensitive enough for quantifying the levels of circulating endothelial cells (mCECs and/or CEPs) in blood samples. These immunoassays provide methods of identifying patients at increased risk from various diseases (e.g., cancer, sickle cell disease, vasculitidis, diabetes, pulmonary hypertension, and cardiovascular disease). The convenient, highly sensitive and rapid means to test blood samples to identify such patients provided by this invention is highly desirable so that preventive measures may be undertaken. Use of electochemiluminescence (ECL)-detection is a preferred means to accomplish this.

This invention is based on combining the high specificity of procedures used to isolate circulating endothelial cells from blood with the high sensitivity of certain immunologically based assays such as ECL. Circulating endothelial cells are first enriched using immunomagnetic beads.

In an embodiment of the detection method of this invention, the immunological assay is such that the assay is capable of detecting antigen from three hundred, more preferably one hundred fifty, more preferably one hundred, more preferably thirty and most preferably ten endothelial cells per milliliter of blood.

The following is a preferred embodiment of a procedure to enrich for endothelial cells:
A blood sample (usually in the range of approximately 8 to 20 ml) is taken from a patient:
  1. Removal of red blood cells.
  2. Optional negative selection to further deplete normal leukocytes. A preferred embodiment includes this step.
  3. Positive selection for circulating endothelial cells (mCECs or CEPs).
  4. Detection and quantification of mCECs or CEPs using an immunoassay for one or more antigens from circulating mCECs or CEPs.

1. Removal of Red Blood Cells.

A variety of methods are available to remove red cells including but not limited to separation based on density (such as collection of blood directly into the Becton Dickinson BD Vacutainer CPT tubes) followed by centrifugation) and commercial lysing buffers such as PURESCRIPT RBC lysis buffer (Gentra, Minneapolis), FACS lysing solution (BDIS), IMMUNOLYSE (Coulter), OPTILYSE B (Immunotech), and ACK lysing buffer (Biosource, Rockville, Md.).

A preferred method uses the BD Vacutainer CPT tubes with anticoagulant (EDTA or citrate). These tubes contain a material that upon correct centrifugation (1,100×g for 10 minutes, swing-out bucket rotor) allows for elimination of red blood cells and neutrophils. After centrifugation, the bottom of the tube contains a cell pellet of erythrocytes (red blood cells) and neutrophils. Above the cell pellet is a gel barrier and above the gel barrier are tumor cells, lymphocytes and monocytes as a band at the bottom of the plasma. The tumor cells, lymphocytes and monocytes can then be readily collected from the top above the gel barrier. This method is preferred as it removes not only the red blood cells but also the neutrophils.

2. Negative Selection to Further Deplete Normal Leukocytes.

A preferred embodiment of this invention uses a negative selection step for isolation of endothelial cells. Negative selection is the selective removal of unwanted cells. Negative selection allows for further depletion of leukocytes especially the lymphocytes and monocytes. One approach is to use magnetic beads with attached antibodies against one or more leukocyte antigens such as CD45 and/or CD3. In a preferred embodiment, more than one antibody against leukocytes is used. Addition of these magnetic beads to the blood sample and removal of the beads with a magnet further depletes the sample from leukocytes and enriches for endothelial cells. Another approach for negative selection comprises the use of antibodies that are bispecific for both leukocyte antigens, especially CD45, the common leukocyte antigen, and for a red blood cell antigen such as glycophorin A. One or more of these bispecific antibodies are added to the BD Vacutainer CPT tubes before blood collection. In a preferred embodiment, the cocktail of bispecific antibodies against more than one leukocyte-associated CD molecule is used. When the blood is introduced into the CPT vacutainer tube, the bispecific antibodies form immunorosettes each consisting of leukocytes plus many red blood cells. These immunorosettes have a density approximately that of red blood cells and when centrifuged are found in the red blood cell pellet, thus further removing leukocytes from the tumor cell fraction found above the cell pellet and gel barrier. The fraction with the tumor cells in plasma is collected for further processing.

3. Positive Selection for Circulating Endothelial Cells (mCECs or CEPs).

The preferred method of isolating circulating endothelial cells uses immunomagnetic beads. Other methods of isolation of circulating cells include filtration (Vona G et al., 2000, Am J. Pathol. 2000 156:57-63). In a preferred embodiment, the immunomagnetic beads have antibodies against antigens found selectively on the surface of endothelial cells. Examples include but are not limited to: a) in the case of CEPs: CD133, VEGFR-2, and CD34; b) in the case of mCECs: CD146, vWF, and CD31. Immunomagnetic beads with antibodies against one of these antigens are used. The immunomagnetic beads may be of various sizes (50 microns to less than 200 nm) and include DYNAL beads (>1.5 microns to about 50 microns). In an embodiment of the invention, EasySep™ positive selection cocktail and EasySep™ Magnetic nanoparticles (Stemcell Technologies) with the one of the above mentioned antibodies are added to the fraction with the endothelial cells from the previous step. A magnet is then used to enrich or isolate endothelial from the rest of the material and the endothelial cells are washed with an aqueous solution.

4. Detection and Quantification of mCECs or CEPs Using an Immunoassay for One or More Antigens from Circulating mCECs or CEPs.

In a preferred embodiment, the isolated or enriched mCECs or CEPs are lyzed before assay and the previously used magnetic beads removed magnetically. For lysis, commercially available cell lysis reagents can be used including, but not limited to: Pierce Lysis Buffer [M-PER® Extraction Reagent (Product number 78501 from Pierce Biotechnology, Inc., Rockford, Ill.)] and Sigma Lysis Buffer [Sigma Cel-Lytic™-M (Sigma Product Number C 2978, Sigma-Aldrich, Inc., St. Louis, Mo. 63103)]. After lysis, cell debris is removed by centrifugation leaving the lysate supernatant with the mCEC or CEP antigens to be measured.

Detection of mCEC or CEP-specific antigens can then be accomplished by use of a highly sensitive sandwich immunoassay using antibodies which bind to the antigen being assayed. A variety of antibodies can be used for the immunoassay, preferably including at least one polyclonal antibody and most preferably, using two polyclonal antibodies. In a preferred embodiment of the invention, one antibody is linked with biotin and the a second antibody against ER is labeled with a detecting molecule In a more preferred embodiment using electrochemiluminescence (ECL), the detecting molecule is ruthenium. There is abundant literature in the public domain provides amply useful methods for linking ruthenium to antibodies (e.g., Lee et al., Am J Trop Med Hyg 2001, 65:1-9). The lysate supernatant is then mixed with the two antibodies and incubated briefly followed by the addition of streptavidin-coated magnetic beads in a solution containing tripropylamine. With application of an electric potential and in the presence of the target antigen (ER), the ruthenium label is excited and light is emitted and detected using an ECL detecting instrument (such as the ORIGEN analyzer or a commercially available instrument like the M-Series® 384 from BIOVERIS Corporation, Gaithersburg, Md.). The ECL signal is proportional to the number of mCECs or CEPs in the original blood sample.

In a preferred embodiment of the invention, the immunoassay utilized in accordance with this invention can use one of the following combinations:

1. Two sets of polyclonal antibodies against the endothelial antigen (the most preferred embodiment)
2. A polyclonal antibody and a monoclonal antibody against the endothelial antigen.
3. Two monoclonal antibodies against the endothelial antigen.

In a preferred embodiment of the invention, the antigen target used for enrichment or isolation of the endothelial cells is different from the antigen target for the sandwich immunoassay. These two antigen targets form an antigen pair; examples of these antigen pairs include:

| Endothelial Cell Type for Assay | Antigen Pair Number | Antigen target for enrichment or isolation using magnetic beads with antibodies against such antigen | Antigen target for sandwich immunoassay |
| --- | --- | --- | --- |
| MCECs | 1 (preferred for mCECs) | vWF | CD146 |
| | 2 | CD146 | vWF |
| | 3 | CD31 | CD146 |
| | 4 | CD31 | vWF |
| CEPs | 1 (preferred for CEPs) | CD133 | VEGFR-2 |
| | 2 | VEGFR-2 | CD133 |
| | 3 | CD34 | CD133 |
| | 4 | CD34 | VEGFR-2 |
| | 5 | VLA-4 (CD49d/ CD29 heterodimer) | LFA-1 (CD11a/ CD18 heterodimer) |
| | 6 | LFA-1 (CD11a/ CD18 heterodimer) | VLA-4 (CD49d/ CD29 heterodimer) |
| | 7 | CD11a | CD146, VEGFR-2, CD133 |
| | 8 | CD11b | CD146, VEGFR-2, CD133 |
| | 9 | CD11c | CD146, VEGFR-2, CD133 |
| | 10 | CD18 | CD146, VEGFR-2, CD133 |
| | 11 | LFA-1 (CD11a/ CD18 heterodimer) | CD146, VEGFR-2, CD133 |
| | 12 | VLA-4 (CD49d/ CD29 heterodimer) | CD146, VEGFR-2, CD133 |
| | 13 | CD146, VEGFR-2, CD133 | CD11a |
| | 14 | CD146, VEGFR-2, CD133 | CD11b |
| | 15 | CD146, VEGFR-2, CD133 | CD11c |
| | 16 | CD146, VEGFR-2, CD133 | CD18 |
| | 17 | CD146, VEGFR-2, CD133 | LFA-1 (CD11a/ CD18 heterodimer) |
| | 18 | CD146, VEGFR-2, CD133 | VLA-4 (CD49d/ CD29 heterodimer) |
| | 19 | CD31(PECAM) | CD146, VEGFR-2, |

| Endothelial Cell Type for Assay | Antigen Pair Number | Antigen target for enrichment or isolation using magnetic beads with antibodies against such antigen | Antigen target for sandwich immunoassay |
|---|---|---|---|
| | 20 | CD141 | CD133 CD146, VEGFR-2, CD133 |
| | 21 | CD105 (Endoglin) | CD146, VEGFR-2, CD133 |
| | 22 | CD144 (VE Cadherin) | CD146, VEGFR-2, CD133 |
| | 23 | tie2 (Angiopoietin 1 receptor) | CD146, VEGFR-2, CD133 |
| | 24 | *Ulex europaeus* lectin | CD146, VEGFR-2, CD133 |
| | 25 | E-selectin | CD146, VEGFR-2, CD133 |

For example, a preferred embodiment for detecting mCECs is to use beads with antibodies against vWF for enrichment or isolation followed by a pair of antibodies against CD146 for detection by sandwich immunoassay. A preferred embodiment for detecting CEPs is to use beads with antibodies against CD133 for enrichment or isolation followed by a pair of antibodies against VEGFR-2 for detection by sandwich immunoassay. Another preferred embodiment for detecting CEPs is to use beads with antibodies against CD34 for enrichment or isolation followed by a pair of antibodies against VEGFR-2 for detection by sandwich immunoassay.

The immunoassay of this invention is more rapid and has a significantly greater sensitivity than any previously developed immunoassay for an endothelial cell antigen. The immunoassay of this invention is capable of detecting antigen from 300 circulating mCECs or CEPs per ml of blood, more preferably from 150 circulating mCECs or CEPs per ml of blood, more preferably from 100 circulating mCECs or CEPs per ml of blood, more preferably from 30 circulating mCECs or CEPs per ml of blood, and most preferably from 10 mCECs or CEPs per ml of blood. In an embodiment of this invention, the assay is capable of detecting the antigen from 4 picograms of antigenic protein, more preferably the assay is capable of detecting the antigen from 1 picogram of antigenic protein.

In another preferred embodiment, the immunoassay of this invention consist of a method of assaying endothelial cells in a blood sample comprising enriching the endothelial cells from the blood sample followed by performing on the enriched endothelial cells an immunoassay capable of detecting VEGFR2 expressed by the endothelial cells and wherein the immunoassay is capable of detecting VEGFR2 from 300 human umbilical vein endothelial cells (HUVECs), more preferably from 150 HUVECs, more preferably from 100 HUVECs, more preferably from 30 HUVECs, and most preferably from 10 HUVECs.

In another preferred embodiment, the immunoassay of this invention consist of a method of assaying endothelial cells in a blood sample comprising enriching the endothelial cells from the blood sample followed by performing on the enriched endothelial cells an immunoassay capable of detecting VEGFR2 expressed by the endothelial cells and wherein the immunoassay is capable of detecting 4 pg of VEGFR2, more preferably 1 pg of VEGFR2, more preferably from 0.3 pg of VEGFR2, and most preferably from 0.1 pg of VEGFR2.

In another preferred embodiment, the immunoassay of this invention consists of a method of assaying an endothelial cell antigen on endothelial cells in a blood sample comprising enriching the endothelial cells from the blood sample followed by performing on the enriched endothelial cells an immunoassay capable of detecting the antigen expressed by the endothelial cells, wherein the immunoassay is capable of detecting the antigen from three hundred endothelial cells per milliliter of blood, more preferably from one hundred fifty endothelial cells per milliliter of blood, more preferably from one hundred endothelial cells per milliliter of blood, more preferably from thirty endothelial cells per milliliter of blood, and most preferably from ten endothelial cells per milliliter of blood.

Besides electrochemiluminescence, other immunoassays that can yield a high sensitivity required for this application include, but are not limited to:
  a) Chemiluminescence such as described by Liu Y et al., 2003 (J Food Protection 66:512-7).
  b) Fluorogenic-chemiluminescence (FCL) as described by Yu H et al., 2000 (Biosens Bioelectron 14:829-40)
  c) Fluoresence polarization immunoassay (see Howanitz J H, 1988 Arch Pathol Lab Med 112:775-9)
  d) Time-resolved fluorescence immunoassay (Butcher H et al., 2003, J Immunol Methods 272:247-56; Soukka et al., 2001, Clin Chem 47:1269-78; Howanitz J H, 1988 Arch Pathol Lab Med 112:775-9)

Due to its sensitivity the method according to this invention for identifying patients at risk for increased disease (including, but not limited to: cancer, sickle cell disease, vasculitidis, pulmonary hypertension, diabetes, and cardiovascular disease) and who are likely to benefit from prophylactic measures to prevent such disease or disease worsening.

The invention will be better understood by reference to the following examples, which illustrate but do not limit the invention described herein.

EXAMPLES

Example 1

A patient comes into the office and a blood sample is collected in a tube to prevent clotting. mCECs are isolated and then lyzed using a lysis buffer. A ruthenium-labeled antibody against an antigen against mCECs and a biotinylated antibody (also against the antigen from mCECs) is added along with a solution of tripropylamine and magnetic beads with avidin attached. An electric current is applied and electrochemiluminescence (ECL) is detected using an ECL detection device such as one commercially available (BioVeris Corporation or Roche Diagnostics). The signal is proportional to the amount of mCECs per ml found in the circulation.

Example 2

Methods as in Example 1, in which mCECs are isolated or enriched using magnetic beads coated with antibodies against vWF. These cells are lysed using Sigma Lysis Buffer [Sigma CelLytic™-M (Sigma Product Number C 2978, Sigma-Aldrich, Inc., St. Louis, Mo. 63103)]. Cell lysis is performed as per the manufacture's recommendation with the addition of 5 minutes of vigorous vortexing prior to cell debris removal. Cell debris is removed from the cell lysate by centrifugation at 14,000 rpm for 30 minutes in an Eppendorf Centrifuge (Model 5415C). A magnet is used to further deplete the magnetic particles. Ruthenium-labeled antibodies against CD-146 and biotinlyated antibodies against CD-146 are added to the lysate and then magnetic strepavidin beads and a solution containing tripropylamine. An electric current is applied and electrochemiluminescence (ECL) is detected using an ECL detection device such as one commercially available (BioVeris Corporation). The signal is proportional to the amount of mCECs and the number of mCECs can be estimated by comparing this signal with the signal from a positive control sample.

Example 3

Methods as in example 2, except that the number of CEPs is determined and the magnetic beads used for isolation or enrichment of CEPs are coated with antibodies against CD133 not vWF and the sandwich ECL immunoassay uses antibodies against VEGFR-2 not CD-146.

Example 4

An assay buffer is prepared: 0.5% Tween-20 and 0.5% bovine serum albumin (BSA) in PBS (phosphate buffered saline).

Antibody against CD 146 is first obtained in both biotinylated and non-biotinylated forms. Biotinylation of antibodies is well-known in the art and can be performed in solution or in solid-phase (Strachan E et al., 2004, J Mol Recognit 17:268-76). Ruthenium labeling ("TAG-label") is performed as follows:
  1.5 µg/µl ruthenium label (BV-TAG-NHS Ester, Catalog #110034; BioVeris Corporation, Gaithersburg, Md., USA) is prepared in DMSO.
  For 500 µl of antibody, 18.8 µl BV-TAG-NHS is added and for 200 µl of polyclonal antibody, 3.8 µl BV-TAG-NHS is added. In each case, the solution is incubated for one hour and the reaction stopped by the addition of 20 µl of 2M glycine.
  Uncoupled BV-TAG-NHS Ester in each reaction mixture is removed using a PD-10 gel filtration column, pre-equilibrated with PBS (including 0.08% sodium azide), which is also used for elution. For each labeled antibody, the protein concentration in each fraction is determined by protein assay and the fractions with high protein content is used in subsequent examples.
The ruthenium-labeled antibody against CD146 and the biotinylated antibody against CD146 are referred hereafter in this example as "TAG-pAb" and "Biotin-pAb".

Endothelial cells [human umbilical vein endothelial cells (HUVEC, Catalog number CC-2517) from Cambrex Corporation, East Rutherford, N.J. 07073] are grown in 6-well tissue culture plates as per manufacturer's recommended conditions, washed two times with PBS, and an aliquot counted using a hemacytometer. These cells are lysed using Sigma Lysis Buffer [Sigma CelLytic™-M (Sigma Product Number C 2978, Sigma-Aldrich, Inc., St. Louis, Mo. 63103)]. Cell lysis is performed as per the manufacture's recommendation with the addition of 5 minutes of vigorous vortexing prior to cell debris removal. Cell debris is removed from the cell lysate by centrifugation at 14,000 rpm for 30 minutes in an Eppendorf Centrifuge (Model 5415C).

An electrochemiluminescence assay is performed as follows:
  Sequentially, to each well, cell lysate supernatants are added (the amount of lysate per well is varied from that extracted from 30 to 100 endothelial cells; control wells without extract are also used) and then 50 µl/well of a mixture of TAG-Ab and Biotin-Ab (e.g., at a concentration between 0.5 to 2 µg/ml each; diluted into the PBS assay buffer) are added to wells of a 96-well U-bottom polypropylene plate and are incubated at room temperature with constant shaking (e.g., for 2 hours).
  10 µg of magnetic streptavidin beads (e.g., Dynabeads M-280 Streptavidin, Catalog #110028, BioVeris, Corporation, Gaithersburg, Md.) in 25 µl is added to each well and incubated with constant shaking (e.g., for 30 minutes).
  PBS assay buffer is added to each well to make a final volume of 250 µl per well. All conditions are tested in at least duplicate wells. The 96 well plate is then analyzed for electrochemiluminescence using the M8 M-Series® Analyzer (Catalog Number 310800, BioVeris, Corporation, Gaithersburg, Md.).

Using this immunoassay, the ECL signal is proportional to the number of HUVEC cells and CD146 is detectable and above baseline from at least 100 HUVEC cells per well.

Example 5

In this example, the sensitivity of detecting recombinant VEGFR2 using a sandwich immunoassay using electrochemiluminescence was examined.
  A PBS assay buffer was prepared:
  Assay Buffer: 0.5% Tween-20 and 0.5% bovine serum albumin (BSA) in PBS (phosphate buffered saline, pH 7.2)
  A standard diluent was prepared:
  Standard Diluent: 1% bovine serum albumin (BSA) in PBS (phosphate buffered saline, pH 7.2)
  Anti-VEGFR2 polyclonal antibody was first obtained in both biotinylated (BAF357 from R&D Systems) and non-biotinylated forms (AF357 from R&D systems). The non-biotinylated polyclonal antibody is ruthenium labeled ("TAG-labeled") according the methods of Lorence & Lu (PCT WO 2006/041959 A2). The ruthenium-labeled polyclonal antibody and the biotinylated polyclonal antibody are referred hereafter in this example as "TAG-pAb" and "Biotin-pAb".
  Recombinant VEGFR2 protein was obtained in the form of VEGFR2-Fc protein (a chimeric protein consisting of the extracellular domain fused to the Fc region of human IgG via a linker group; R&D systems, catalog #357-KD).

An electrochemiluminescence assay was performed as follows:
  Standards were diluted in 1 ml PBS (pH 7.2 with 0.1% BSA and 0.05% sodium azide) to form a stock solution of 50 µg/mL.
  Standards were diluted in Standard Diluent to yield 1600, 160, 16, and 4 pg/well when 25 µL was used per well. To each well of a 96-well U-bottom polypropylene plate (with 25 µL of standard per well) were added 50 µl/well of a mixture of TAG-Ab and Biotin-Ab (e.g., at a concentration of 1.0 µg/ml in the 50 µl prior to addition) and the resultant solution was incubated at room temperature with constant shaking (for 2 hours).
  10 µg of magnetic streptavidin beads (e.g., Dynabeads M-280 Streptavidin, Catalog #110028, BioVeris Corporation, Gaithersburg, Md.) in 25 µl was added to each well and incubated with constant shaking (for 30 minutes).
  PBS Assay Buffer was added to each well to make a final volume of 250 µl per well. All conditions were tested in at least duplicate wells. The 96 well plate was then analyzed for electrochemiluminescence using the M-Series® 384 Analyzer (BioVeris Corporation, Gaithersburg, Md.).

Using this immunoassay, as little as 4 pg per well of VEGFR2 standard was detectable with a signal above background (Table 1).

TABLE 1

Electrochemiluminescence (ECL) detection of recombinant VEGFR2 by immunoassay using ruthenium-labeled polyclonal (TAG-pAb) and biotinylated polyclonal antibody (Biotin-pAb).

| VEGFR2 (pg/well) | Mean ECL Signal (above background)* |
|---|---|
| 4 | 722 |
| 16 | 1957 |
| 160 | 13021 |
| 1600 | 113347 |

*Mean ECL signal above the mean signal from control wells with no antigen.

Example 6

In this example, the specificity for an ECL immunoassay against VEGFR2 for detecting VEGFR2 from endothelial cells vs. non-endothelial cells was determined along with a repeat determination of the sensitivity of detecting recombinant EGFR. Methods were as that used in example 5 with (1) the testing of lower amounts of VEGFR2 standard; and (2) the additional analysis of cell extracts from HUVEC cells (positive control cells for VEGFR2 expression) and K562 human leukemia (negative for VEGFR2).

HUVECs [Catalog number CC-2517] from Cambrex Corporation, East Rutherford, N.J. 07073] were grown in tissue culture as per manufacturer's recommended conditions (and did not include VEGF), washed two times with PBS, and an aliquot counted using a hemacytometer. K562 cells (from ATCC, Manassas, Va.) were grown in tissue culture plates as per ATCC recommended conditions, washed two times with PBS, and an aliquot counted using a hemacytometer. Lysis of HUVEC and K562 cells and obtaining the supernatant was performed using Pierce RIPA Buffer [catalog #89900, Pierce Biotechnology, Rockford, Ill.] with Pierce protease inhibitor [catalog #78410; Pierce Biotechnology] as per manufacturer's recommended conditions. The amount of lysate supernatant per well was varied from that extracted from 300, 625, 2500 and 10,000 cells and analyzed for VEGFR2 using the immunoassay described in Example 5.

Using the VEGFR2 standard, as little as 1 pg per well of EGFR standard was detectable with a signal above background (Table 2).

TABLE 2

Electrochemiluminescence (ECL) detection of recombinant VEGFR2 by immunoassay using ruthenium-labeled polyclonal (TAG-pAb) and biotinylated polyclonal antibody (Biotin-pAb).

| VEGFR2 (pg/well) | Mean ECL Signal (above background)* |
|---|---|
| 1 | 504 |
| 4 | 1706 |
| 16 | 6289 |
| 160 | 26023 |
| 1600 | 91935 |

*Mean ECL signal above the mean signal from control wells with no antigen.

Figure 1:
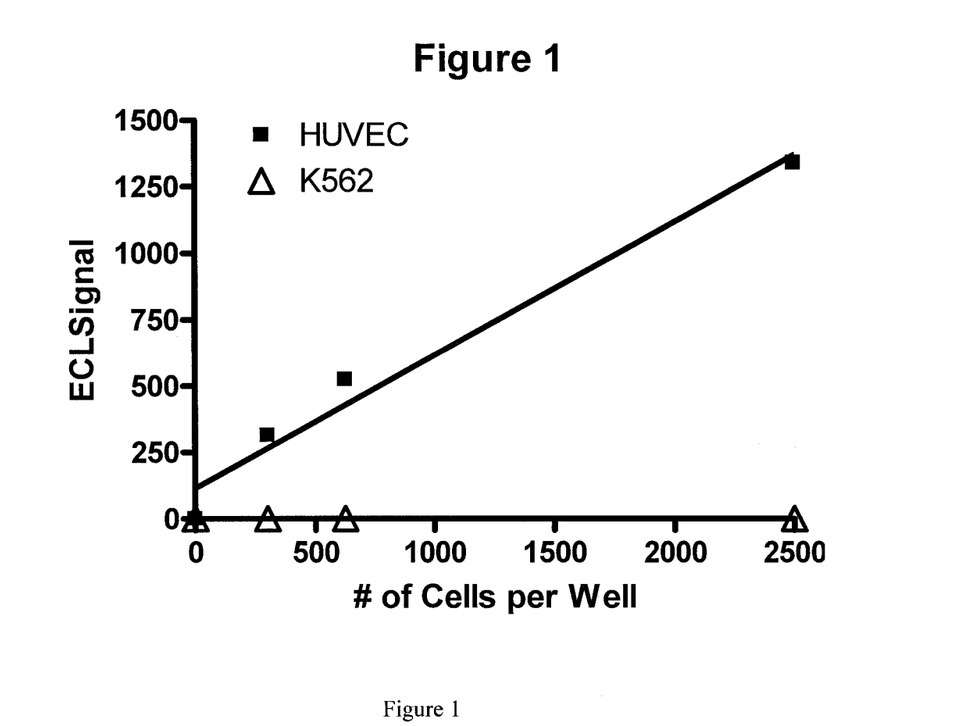
FIG. 1. Sensitivity for Detecting VEGFR2. Shown is a comparison of the ECL signal for the immunoassay detection of VEGFR2 in lysates from HUVEC cells (endothelial cells which are a positive control for VEGFR2 expression) versus K562 (negative control for VEGFR2 expression). Shown is the data using lysates from 300, 625 and 2500 cells per well.
Figure 2:
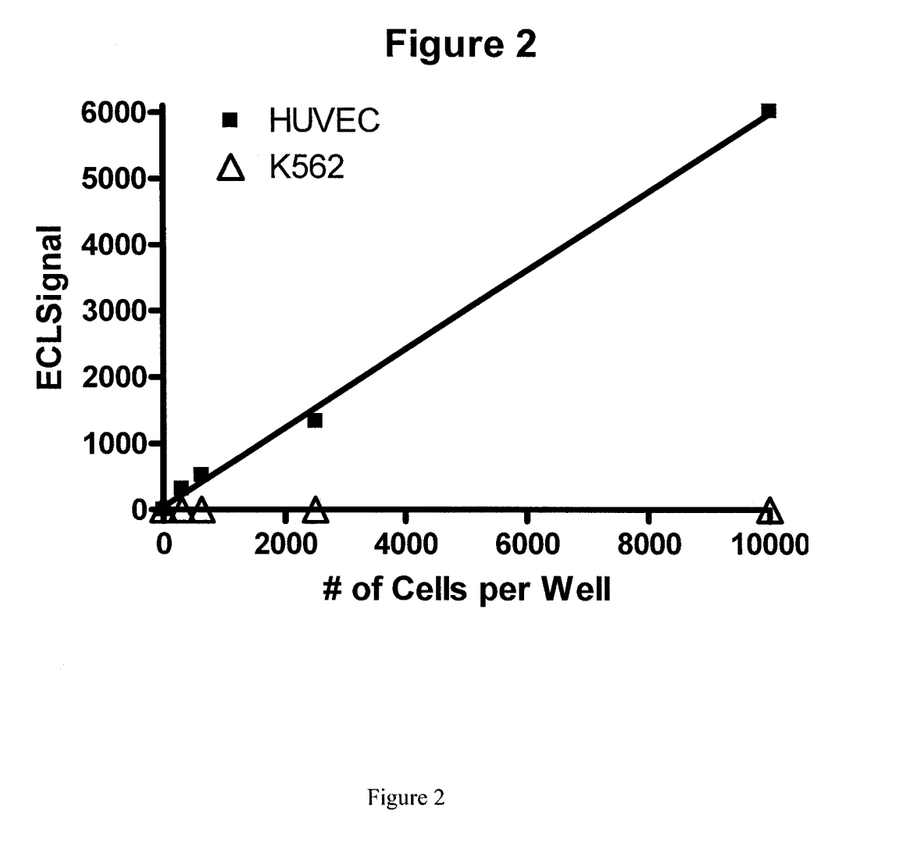
FIG. 2. Sensitivity and Specificity for Detecting VEGFR2 from Endothelial Cells vs. Non-Endothelial Cells. Shown is a further comparison of the ECL signal for the immunoassay detection of VEGFR2 in lysates from HUVEC cells (endothelial cells which are a positive control for VEGFR2 expression) versus K562 (negative control for VEGFR2 expression). Data from the same experiment as shown in FIG. 1 is used for this figure, except that data obtained from lysate material from 10,000 cells per well were also included in this graph in order to display an increased X-axis scale.

Using cell lysates, the results from this experiment are presented in FIGS. 1 and 2. FIG. 1 graphically displays the lower end of the data set to best see the ability of this assay to detect VEGFR2 from low cell numbers. FIG. 1 only includes data for the cell range up to 2500 cells per well. FIG. 2 graphically displays the entire data set (up to 10,000 cells per well).

VEGFR2 was detectable and above baseline from lysates from HUVEC cells in this experiment including those wells using the lowest amount of HUVEC lysate in this experiment (lysate from 300 cells added per well; FIG. 1). Furthermore, the lysate from the HUVEC cells (endothelial cell positive control for VEGFR2 expression) gave a much higher signal in the immunoassay for VEGFR2 than the lysate from K562 cells (negative for VEGFR2 expression) over the entire tested range from 300 to 10,000 cells per well and all of the lysates from K562 cells were negative indicating the high sensitivity and specificity of the results for VEGFR2 detection (FIGS. 1 & 2).

Example 7

In this example, the sensitivity for an ECL immunoassay against VEGFR2 for detecting VEGFR2 from HUVEC endothelial cells was further examined. Methods were as that used in example 6 with the testing of lower amounts of cell extracts from HUVEC cells (positive control cells for VEGFR2 expression).

Using the lysates from HUVEC endothelial cells, lysates from as little as 150 HUVECs per well was detectable with a signal above background (Table 3).

TABLE 3

Electrochemiluminescence (ECL) detection of VEGFR2 from HUVEC lysates by immunoassay using ruthenium-labeled polyclonal (TAG-pAb) and biotinylated polyclonal antibody (Biotin-pAb).

| Cells per Well | Mean ECL Signal (above background)* |
|---|---|
| 150 | 207 |
| 200 | 261 |
| 300 | 338 |
| 625 | 504 |
| 2500 | 824 |

*Mean ECL signal above the mean signal from control wells with no antigen.

Example 8

In this example, the ECL signals from an immunoassay against VEGFR2 was determined for small numbers of human peripheral blood mononuclear cells (PBMCs). Methods to test cell lysates as in Example 6 were used except that lysates of human PBMCs were used. Human PBMCs were obtained from Cellular Technology Ltd.; Cleveland, Ohio; product #CTL-UP1). Lysates from 156, 313, 625, 1250 and 1500 PMBCs were tested in the ECL immunoassay for VEGFR2 as described in Example 7.

Figure 3:
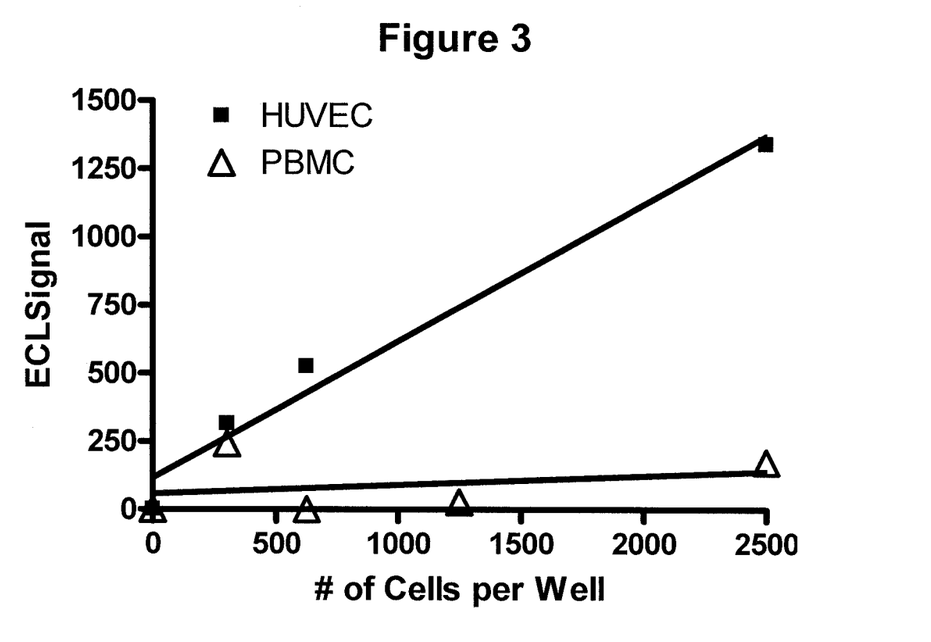
FIG. 3. Specificity for Detecting VEGFR2 from Endothelial Cells vs. Non-Endothelial Cells. Shown is a comparison of the ECL signal for the immunoassay detection of VEGFR2 in lysates from HUVEC cells (endothelial cells which are a positive control for VEGFR2 expression) versus PMBCs. Shown is the data using lysates up to 2500 cells per well.

FIG. 3 shows the results and for comparison purposes the data from Example 6 using HUVECs are included in this graph. For the entire range of PBMCs tested the signal was low or at background levels. These results were consistent with the fact that endothelial cells would not be expected to be found in the maximum amount of PBMCs tested (2500). As indicated in the Background section, CEPs and mCECs represent a very small fraction of mononuclear cells in the blood with an estimate of between 0.01% and 0.0001% (Khan SS et al., 2004). The results from this experiment demonstrate that if there are small numbers of contaminating PBMCs in an enriched population of endothelial cells, these contaminating PBMCs would not give rise to a signal that would prevent the determination of endothelial cell antigens from such an enriched endothelial cell population.

Example 9

In this example, the effectiveness of enrichment was determined. In this example the ability to detect VEGFR2 from cells following enrichment of a hematopoietic cell sample for CD34+ cells was tested twice using immunomagnetic beads. As noted previously, EPCs express both CD34+ and VEGFR2. Therefore enrichment for CD34+ would be expected to enrich for cells with VEGFR2 expression. A Direct CD34 Progenitor Cell Isolation Kit (now called CD34 MicroBead Kit) was obtained from Miltenyi Biotec Inc. (Auburn, Calif.) and used per manufacturer's instructions. This kit contains MicroBeads which are conjugated to the monoclonal mouse anti-human CD34 antibody, QBEND/10. As starting cells for CD34 isolation, cultures of human cord blood (from Cambrex (East Rutherford, N.J., Catalog #2C-101A) were used and were grown in StemSpan Serum Free medium (Stem Cell Technologies; www.stemcell.com) with the following growth factors, all from PeproTech (Rocky Hill, N.J.): human vascular endothelial growth factor (VEGF; 50 ng/ml; catalog number 100-20), human thrombopoietin (20 ng/ml; catalog number 300-18); human interleukin-6 (20 ng/ml; catalog number 200-06), human Fms-related tyrosine kinase 3 ligand (Flt-3; 100 ng/ml; catalog number 300-19) and human stem cell factor (SCF; 100 ng/ml catalog number 300-07). The effect on the expression level of VEGFR2 per cell from culturing the cells in the presence of the ligand (VEGF) for this receptor was not determined.

Lysates (performed as in Example 6 using RIPA or with the addition of the use of Pierce M-PER Mammalian Protein Extraction Reagent, Pierce catalog number 78501) from up to 250,000 cells from two cultures of these human cord blood were analyzed for VEGFR2 expression using the ECL immunoassay as described in Example 5.

Figure 4:
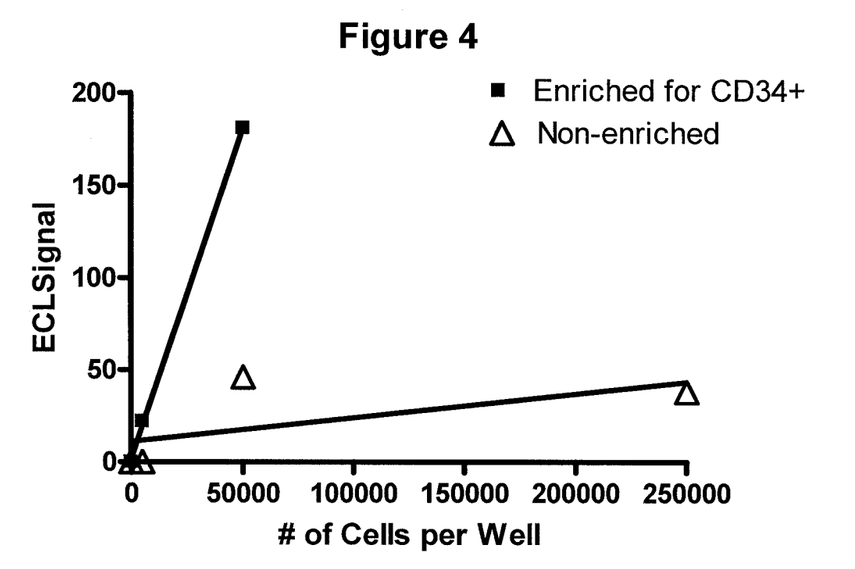
FIG. 4. Effect of enrichment. Comparison of the ECL signal for the immunoassay detection of VEGFR2 in lysates from either non-enriched human cord blood ex vivo cultures or from the same cultures enriched for CD34 antigen using immunomagnetic beads with anti-CD34 antibody. In this figure, cells were extracted using M-PER Pierce Extraction Reagent as indicated in Example 9. Using flow cytometry, it was estimated that there were 960 VEGFR2 positive cells per 5000 CD34 enriched cells.
Figure 5:
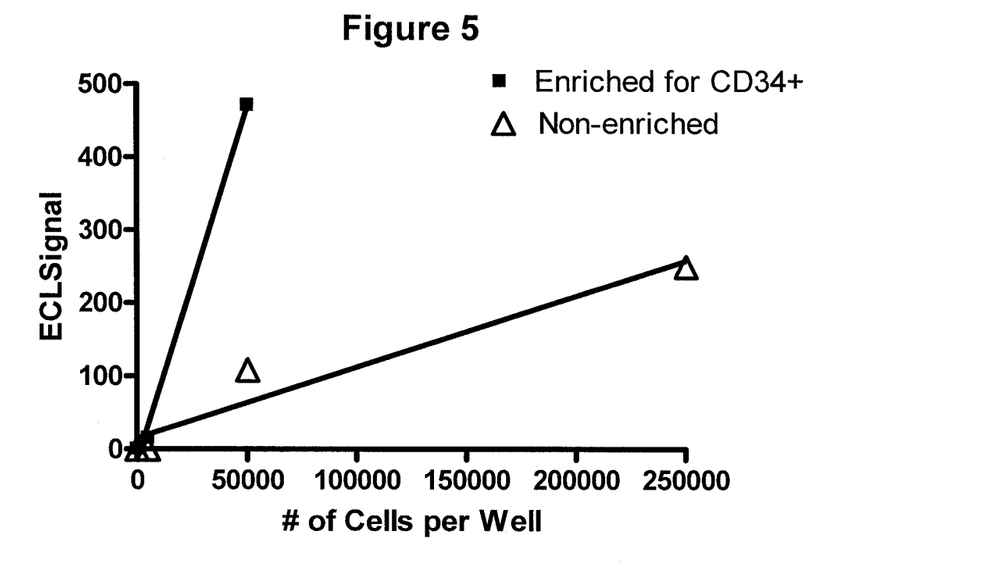
FIG. 5. Effect of enrichment. Comparison of the ECL signal for the immunoassay detection of VEGFR2 in lysates from either non-enriched human cord blood ex vivo cultures or from the same cultures enriched for CD34 antigen using immunomagnetic beads with anti-CD34 antibody. In this figure, the same cells as used to obtain lysates in FIG. 4 were used, except that cells were extracted using RIPA Extraction Buffer as indicated in Example 9.
Figure 6:
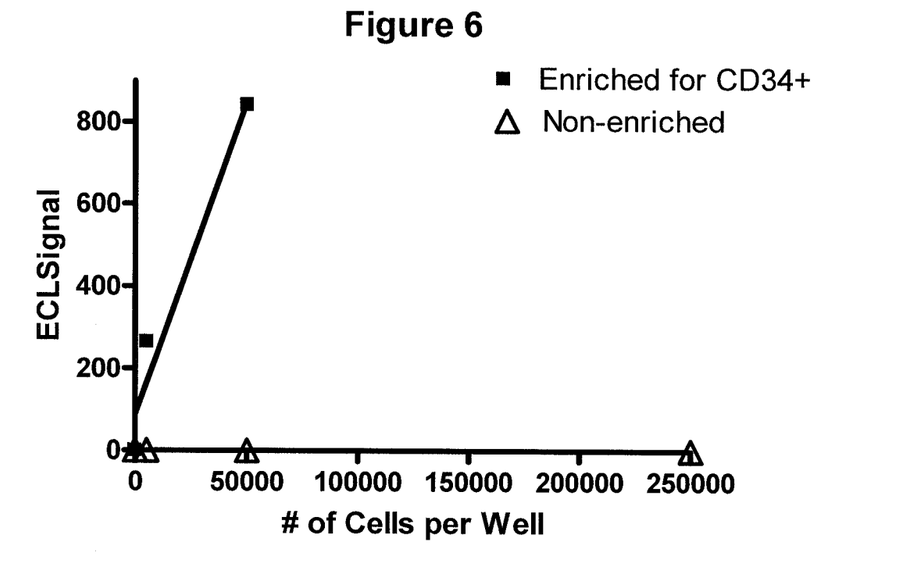
FIG. 6. Effect of enrichment. Comparison of the ECL signal for the immunoassay detection of VEGFR2 in lysates from either non-enriched human cord blood ex vivo cultures or from the same cultures enriched for CD34 antigen using immunomagnetic beads with anti-CD34 antibody. In this figure, a different set of cells from the ex vivo culture of cord blood was used. As in FIG. 4, cells were lysed using the M-Per Pierce Extraction Reagent. Using flow cytometry, it was estimated that there were 700 VEGFR2 positive cells per 5000 CD34 enriched cells.

Results from this experiment are shown in FIGS. 4-6. FIGS. 4-6 all indicate that enrichment using immunomagnetic beads against CD34 antigen was markedly successful at enriching for cells expressing the endothelial cell marker VEGFR2.

This was true regardless of the method of making the cell lysates, although higher signals were obtained using the RIPA buffer (compare FIG. 4 with M-PER lysis buffer vs. FIG. 5 using RIPA) when using the exact same set of cells for extraction.

What is claimed is:

1. A method of assaying endothelial cells in a blood sample comprising enriching the endothelial cells from the blood sample by contacting the blood sample with immunomagnetic beads capable of binding selectively to the endothelial cells, lysing the enriched endothelial cells, followed by performing on the endothelial cell lysate an electrochemiluminescence immunoassay capable of detecting an antigen expressed by the endothelial cells;
    wherein the immunoassay has a sensitivity defined by being capable of detecting the endothelial cell antigen from three hundred endothelial cells per milliliter of blood or by being capable of detecting the endothelial cell antigen from one hundred sixty picograms of antigenic protein; and
    wherein the immunoassay generates an electrochemiluminescence signal proportional to the number of endothelial cells present in the blood sample.

2. The method of claim 1, wherein the immunoassay is capable of detecting the endothelial cell antigen from one hundred fifty endothelial cells per milliliter of blood.

3. The method of claim 1, wherein the immunoassay is capable of detecting the endothelial cell antigen from thirty endothelial cells per milliliter of blood.

4. The method of claim 1, wherein the immunoassay is capable of detecting the endothelial cell antigen from four picograms of antigenic protein.

5. The method of claim 1, wherein the immunoassay is capable of detecting the endothelial cell antigen from one picogram of antigenic protein.

6. The method of claim 1, wherein the endothelial cells are selected from the group consisting of mature circulating endothelial cells and circulating endothelial progenitor cells.

7. The method of claim 6 wherein said endothelial cells are mature circulating endothelial cells and the endothelial cell antigen is selected from the group consisting of CD146 and von Willebrand factor.

8. The method of claim 6 wherein said endothelial cells are circulating endothelial progenitor cells and the endothelial cell antigen is selected from the group consisting of vascular endothelial growth factor receptor-2 and CD133.

9. The method of claim 1, wherein the immunoassay uses a polyclonal antibody against the endothelial cell antigen.

10. The method of claim 1, wherein the immunoassay uses a monoclonal antibody against the endothelial cell antigen.

* * * * *

UNITED STATES PATENT AND TRADEMARK OFFICE
CERTIFICATE OF CORRECTION

| | | |
|---|---|---|
| PATENT NO. | : 8,557,531 B2 | Page 1 of 1 |
| APPLICATION NO. | : 12/296476 | |
| DATED | : October 15, 2013 | |
| INVENTOR(S) | : Lorence | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this
Tenth Day of March, 2015

Michelle K. Lee
*Deputy Director of the United States Patent and Trademark Office*